United States Patent
Galbraith et al.

(10) Patent No.: US 11,318,237 B2
(45) Date of Patent: May 3, 2022

(54) INTEGRATED EXTRACORPOREAL OXYGENATION AND $CO_2$ REMOVAL WITH VENTILATION SYSTEM

(71) Applicants: Separation Design Group LLC, Waynesburg, PA (US); Belluscura LLC, Plano, TX (US)

(72) Inventors: Stephen Douglas Galbraith, Waynesburg, PA (US); Robert M. Rauker, Plano, TX (US)

(73) Assignees: SEPARATION DESIGN GROUP LLC, Waynesburg, PA (US); BELLUSCURA LLC, Plano, TX (US)

( * ) Notice: Subject to any disclaimer, the term of this patent is extended or adjusted under 35 U.S.C. 154(b) by 0 days.

(21) Appl. No.: 17/428,654

(22) PCT Filed: Feb. 6, 2020

(86) PCT No.: PCT/US2020/017015
§ 371 (c)(1),
(2) Date: Aug. 5, 2021

(87) PCT Pub. No.: WO2020/163596
PCT Pub. Date: Aug. 13, 2020

(65) Prior Publication Data
US 2022/0047791 A1 Feb. 17, 2022

Related U.S. Application Data

(60) Provisional application No. 62/826,285, filed on Mar. 29, 2019, provisional application No. 62/801,968, filed on Feb. 6, 2019.

(51) Int. Cl.
*A61M 1/16* (2006.01)
*A61M 1/36* (2006.01)
(Continued)

(52) U.S. Cl.
CPC ........ *A61M 1/1698* (2013.01); *A61M 1/3659* (2014.02); *A61M 1/3663* (2013.01);
(Continued)

(58) Field of Classification Search
CPC .............. A61M 1/1698; A61M 1/3659; A61M 1/3663; A61M 16/0066; A61M 16/06;
(Continued)

(56) References Cited

U.S. PATENT DOCUMENTS

| 5,570,483 | A | 11/1996 | Williamson |
| 6,113,869 | A | 9/2000 | Jain et al. |

(Continued)

OTHER PUBLICATIONS

Is Extracorporeal Circulation the Future of Acute Respiratory Distress Syndrome Management—Combes, et al, Critical Care Perspective, Mar. 13, 2017.

*Primary Examiner* — Philip R Wiest
(74) *Attorney, Agent, or Firm* — Panitch Schwarze Belisario & Nadel LLP

(57) ABSTRACT

A transportable extracorporeal system includes a housing, a blood flow inlet, a blood flow outlet, a plurality of hollow gas permeable fibers, a gas inlet in fluid connection with inlets of the plurality of hollow gas permeable fibers, a gas outlet in fluid connection with outlets of the plurality of hollow gas permeable fibers, a first moving element, a concentrated oxygen generating device, a second moving element, a hollow transport conduit having a proximal opening and a distal opening and a power source configured to provide power to the first and second moving elements. The plurality of hollow gas permeable fibers comprising a gas transfer membrane. The concentrated oxygen generating device is configured to recycle waste oxygen from the gas transfer membrane to increase throughput and remove, by an adsorption/desorption process, unwanted gasses.

19 Claims, 10 Drawing Sheets

(51) Int. Cl.
*A61M 16/06* (2006.01)
*B01D 53/04* (2006.01)
*A61M 16/00* (2006.01)
*B01D 53/22* (2006.01)

(52) U.S. Cl.
CPC ........ *A61M 16/0066* (2013.01); *A61M 16/06* (2013.01); *B01D 53/04* (2013.01); *A61M 2205/3331* (2013.01); *A61M 2205/8206* (2013.01); *B01D 2053/224* (2013.01)

(58) Field of Classification Search
CPC .. A61M 2205/3331; A61M 2205/8206; B01D 53/04; B01D 2053/224
See application file for complete search history.

(56) References Cited

U.S. PATENT DOCUMENTS

| | | |
|---|---|---|
| 2007/0028770 A1 | 2/2007 | Tyndall et al. |
| 2009/0082687 A1 | 3/2009 | Onishi |
| 2013/0157248 A1 | 6/2013 | Fishman et al. |
| 2015/0314059 A1* | 11/2015 | Federspiel ............. A61M 1/32 600/16 |
| 2017/0021302 A1* | 1/2017 | Galbraith ............. B01D 53/053 |
| 2017/0333652 A1 | 11/2017 | Schindhelm et al. |
| 2017/0361052 A1 | 12/2017 | Taylor et al. |
| 2018/0264184 A1 | 9/2018 | Jeffries et al. |
| 2019/0022300 A1 | 1/2019 | Federspiel et al. |

* cited by examiner

INTEGRATED EXTRACORPOREAL OXYGENATION AND CO$_2$ REMOVAL WITH VENTILATION SYSTEM

CROSS-REFERENCE TO RELATED APPLICATIONS

The present application is a Section 371 national phase application of International Patent Application No. PCT/US2020/017015, filed Feb. 6, 2020 and titled, "Integrated Extracorporeal Oxygenation and CO2 Removal with Ventilation System and claims the benefit of U.S. Provisional Patent Application Nos. 62/826,285, filed Mar. 29, 2019 and titled, "Integrated ExtraCorporeal Oxygenation and CO$_2$ Removal and Ventilation System" and 62/801,968, filed on Feb. 6, 2019 and titled "Encorporeal Membrane Oxygenation Device, System and Related Methods" the entire contents of which are incorporated herein by reference in their entirety.

BACKGROUND OF THE INVENTION

Extracorporeal life support ("ECLS") has become increasingly popular as a salvage strategy for critically ill patients. Major advances in technology and the severe acute respiratory distress syndrome that characterized the 2003 severe acute respiratory syndrome ("SARS") coronavirus outbreak, the 2009 influenza A ("H1N1") pandemic, the 2012 middle east respiratory syndrome ("MERS") and the 2019 novel coronavirus outbreak have stimulated renewed interest in the use of venovenous extracorporeal membrane oxygenation ("ECMO") and extracorporeal carbon dioxide removal ("ECCO$_2$R") to support the respiratory system. Potential advantages of ECLS for respiratory failure include the ability to rest the lungs by avoiding injurious mechanical ventilator settings and the potential to facilitate early mobilization, which may be advantageous for bridging to recovery or to lung transplantation. The therapy is now being tested in clinical trials, although numerous questions remain about the application of ECLS and its impact on outcomes in critically ill adults.

Referring to FIGS. 1 and 2, a basic circuit of the prior art ECMO system 1 is composed of a blood pump 4, a membrane lung or gas blender 5, a heat exchanger 6, a medication introduction device 8 and cannulas and tubing 7, as well as an alternative blower 9 to assist the patient's ventilation for introduction of air through a tube 3. A veno-venous ("VV") configured circuit, vein to vein, with a low-flow pump, can partially support the respiratory system by effectively removing carbon dioxide ("CO$_2$").

Roller and centrifugal pumps are the two basic types of blood pumps used for ECLS, although in recent years adults are typically supported with centrifugal technology. A roller pump displaces blood through flexible tubing located inside a curved raceway to generate forward flow proportional to the pump speed and tubing size. This requires careful servo-regulation of pressures and a larger footprint and is generally inadequate for supporting adults over the longer term. Centrifugal pumps generate a pressure differential across the pump head via spinning pump components and centrifugal force, resulting in negative pressure in the drainage tubing and subsequent blood flow. The relationship between pump speed and blood flow is not directly related, requiring a flow meter. Modern pumps use magnetically driven or magnetically suspended impellers, which spin at the desired revolutions per minute to create blood flow while minimizing heat generation and blood-surface contact and therefore hemolysis. Inlet pressure from the drainage limb and outlet pressure from the pump are monitored for excess negative or positive swings, respectively. Additional shunts (e.g., "bridges") between drainage and return limbs for weaning trials) and monitors (e.g., bubble detectors) can be added, but doing so may introduce additional access points and complicate the circuit.

The oxygenator or membrane lung is responsible for gas exchange (FIG. 1). Oxygenation capacity is dependent on the surface area of the membrane and contact with the blood phase. Oxygenator designs have evolved over time from flat sheets to hollow fiber (gas phase inside) membranes and from microporous to compressed microporous ("solid") designs such that gas exchange occurs entirely by diffusion. Polymethylpentene hollow-fiber devices are best suited for longer-term ECLS and have been shown to have lower rates of hemolysis, better durability with lower pressure differential, and less plasma leakage. Fresh gas, or sweep gas, is introduced into the gas phase of the membrane (usually delivered as high concentration oxygen, oxygen-ambient air, or oxygen-CO$_2$ mixtures, controlled by a blender) and is adjusted to lower or maintain CO$_2$ levels. Examples of oxygenator designs include those shown in US Patent Application Publication Nos. 2019/0022300 and 2018/0264184.

Cannulas and tubing size limit the flow rate achieved, which depends directly on the length and inversely on the radius of the conduits. For adults, typical cannulas range from twenty-three to twenty-nine French (23-29 Fr) for venous drainage and twenty-one to twenty-three French (21-23 Fr) for blood return (and as small as seventeen to nineteen French (17-19 Fr) when in a venous-artery ("VA") configuration) with expected pressure flow characteristics available from the manufacturers. Vascular access can be obtained with extrathoracic percutaneous cannulation using the Seldinger technique, although central cannulation and/or a direct cutdown approach are also possible. The femoral vessels usually provide adequate access; a small distal perfusion cannula may be added to avoid or rescue limb ischemia. Alternative arterial access has been achieved in the subclavian and axillary arteries with adjunct synthetic grafting in adults. A double-lumen cannula, which may have a diameter of twenty to thirty-one French (20-31 Fr), with drainage ports in the inferior and superior venae cavae and a return port positioned in the right atrium with flow directed across the tricuspid valve is available for VV-ECMO and offers single-site internal jugular access. In the United States, circuit components are currently approved for use by the Food and Drug Administration for short-term, approximately six hour (6 hrs.), cardiopulmonary bypass.

The goal of ECLS is to support gas exchange and systemic metabolic demands by providing oxygen delivery to the tissues. The degree of support provided for native heart or lung function is in large part dependent on blood flow, as well as patient hemoglobin, inlet hemoglobin saturation, and the properties of the membrane lung.

In the VV configuration, as opposed to VA configuration, ventricular filling pressures and hemodynamics are unchanged in the steady state, but oxygen and carbon dioxide are exchanged via the membrane lung. Because both the drainage and return cannula are positioned in the venous system, mixing can occur. Recirculation, which is the combination of perfusate (oxygenated) blood and the patient's venous blood reinfused into the circuit, can limit oxygen delivery. Here, the lungs sit in series (i.e., supraoxygenated perfusate blood is delivered back to the patient's venous system or right atrium and then traverses the pulmonary circulation) such that expected arterial oxygen saturations are lower, such as greater than eighty-five percent (>85%), depending on the patient's innate pulmonary function. In this setting, adequate oxygen delivery can be maintained, provided cardiac output is sufficient, and especially because cardiac output may be augmented by limiting or removing positive pressure ventilation. $CO_2$ removal is more efficient than oxygenation and thus requires substantially lower flow rates, smaller or pumpless systems, and smaller cannulas.

Systemic anticoagulation, usually with unfractionated heparin, is initiated typically at the time of cannulation to prevent circuit (and patient) thrombosis. The ideal anticoagulation strategy and appropriate tests for monitoring (e.g., activating clotting time, anti-factor Xa or heparin assays, activated partial thromboplastin time, thromboelastography) in ECLS are controversial and should be based on laboratory capabilities and institutional standards.

Currently, a number of companies and research entities have been developing extracorporeal carbon dioxide removal ("$ECCO_2R$") and ECLS systems focused on relieving the workload on a patient's lung while the lung heals or recovers from a respiratory event such as acute respiratory distress syndrome ("ARDS"), viral infection, e.g., SARS virus, H1N1 virus, MERS virus, coronavirus, pneumonia, or other distressing respiratory events. The companies, e.g., A-Lung, HemoVent, etc., have focused on $CO_2$ removal as the key factor in reducing the workload on the lung. The $ECCO_2R$ and ECLS systems developed in the prior art, however, lack portability while also failing to provide integrated passive or minimally invasive ventilation. The systems being developed now do not provide an integrated passive or non-invasive ventilation source for the patient nor do they provide for a renewable, self-generating oxygen source. The current systems, therefore, are dependent on a separate ventilation system and oxygen sourced from finite or fixed volume oxygen sources such as an oxygen cylinder. This can be a very dangerous situation in aircraft when a patient must be transported or any situation when the fixed volume of oxygen may become empty during use.

To be truly portable, the system should be battery powered, possess a self-contained oxygen generating device such as a portable oxygen concentrator ("POC"), utilize the POC's oxygen source to sweep $CO_2$ from the oxygenator, utilize the same POC oxygen source to provide oxygen to the patient's blood through the oxygenator, recycle the sweep gas back through the POC where the carbon dioxide, Argon and other gases are removed, while also providing integrated passive, non-invasive ventilation separately or with mixed concentrated oxygen from the POC. The preferred device also preferably includes control or a central processor to control oxygen concentration and pressures introduced to the patient's lungs, oxygenation and $CO_2$ removal from the patient's blood, production of concentrated oxygen and related components of the system, based on data acquired from sensors connected to the system and central processor.

Mechanical ventilation (MV) is the cornerstone of acute respiratory distress syndrome ("ARDS") management. It guarantees sufficient alveolar ventilation, high FiO2 concentration, and high positive end-expiratory pressure levels. However, experimental and clinical studies have accumulated, demonstrating that MV also contributes to the high mortality observed in patients with ARDS by creating ventilator-induced lung injury. Under these circumstances, extracorporeal lung support (ECLS) may be beneficial in two distinct clinical settings: to rescue patients from the high risk for death associated with severe hypoxemia, hypercapnia, or both not responding to maximized conventional MV, and to replace MV and minimize/abolish the harmful effects of ventilator-induced lung injury. High extracorporeal blood flow venovenous extracorporeal membrane oxygenation (ECMO) may therefore rescue the sickest patients with ARDS from the high risk for death associated with severe hypoxemia, hypercapnia, or both not responding to maximized conventional MV. Successful venovenous ECMO treatment in patients with extremely severe H1N1-associated ARDS and positive results of the CESAR trial have led to an exponential use of the technology in recent years. Alternatively, lower-flow extracorporeal CO2 removal devices may be used to reduce the intensity of MV (by reducing Vt from 6 to 3-4 ml/kg) and to minimize or even abolish the harmful effects of ventilator-induced lung injury if used as an alternative to conventional MV in nonintubated, nonsedated, and spontaneously breathing patients. Is Extracorporeal Circulation the Future of Acute Respiratory Distress Syndrome Management? Combes et al, American Journal of Respiratory and Critical Care Medicine, May 1, 2017

BRIEF SUMMARY OF THE INVENTION

Briefly, a preferred embodiment, of the present invention is directed to an extracorporeal system for lung assist including an outer casing or housing, a blood flow inlet in fluid connection with the housing, a blood flow outlet in fluid connection with the housing and a plurality of hollow gas permeable fibers adapted to permit diffusion of gas between blood and an interior of the hollow gas permeable fibers. The plurality of hollow gas permeable fibers are positioned between the blood flow inlet and the blood flow outlet such that blood flows around the plurality of hollow gas permeable fibers when flowing from the blood flow inlet to the blood flow outlet. The plurality of hollow gas permeable fibers extends generally perpendicular to the direction of bulk flow of blood through the housing. The assembly includes a gas transfer membrane. The extracorporeal system also includes a gas inlet in fluid connection with the housing and in fluid connection with inlets of the plurality of hollow gas permeable fibers, a gas outlet in fluid connection with the housing and in fluid connection with outlets of the plurality of hollow gas permeable fibers, at least one moving element to create velocity fields in blood flow contacting the plurality of hollow gas permeable fibers and a concentrated oxygen generating device. The oxygen generating device is capable of generating concentrated oxygen from ordinary air. The at least one moving element is comprised of a pump. The oxygen generating device has at least one outlet port and at least one inlet port. A first at least one outlet port is in fluid connection with the gas inlet. The first at least one inlet port is in fluid connection to the gas outlet. The concentrated oxygen generating device is capable of recycling the waste oxygen from the gas transfer membrane to increase its throughput and is capable of selectively removing, by an adsorption/desorption process, unwanted gasses such as $CO_2$, argon, water vapor, and nitrogen.

The preferred system also preferably includes a second at least one outlet port and a second at least one inlet port. The port provides access to air outside the housing. A second moving element is configured for moving gases, fluids and vapors. The second moving element has at least one intake port and at least one outtake port and is comprised of a compressor. A hollow transport conduit has a proximal opening and a distal opening. The proximal opening is in fluid connection with a first at least one outtake port. A power source, preferably a battery, provides power to the first and second moving elements. The battery is preferably removable and replaceable relative to the housing and is rechargeable.

The preferred system is portable and provides concentrated oxygen. The system includes a sieve module with layers of zeolites for adsorbing Nitrogen, $CO_2$ and Argon. In the preferred embodiment, the sieve module includes three separate modules. The system is preferably modular such that different cartridges could be designed that instruct the system regarding available flow of oxygen concentrations. The system provides sweep gas, oxygen and recycles the sweep gas as described herein and in previous applications. The system may incorporate any aspect of the systems and its features described in International Patent Application No. PCT/US2017/023990 and U.S. Pat. Nos. 8,894,751, 9,199,055 and 9,839,757, each of which is incorporated herein by reference in their entirety.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
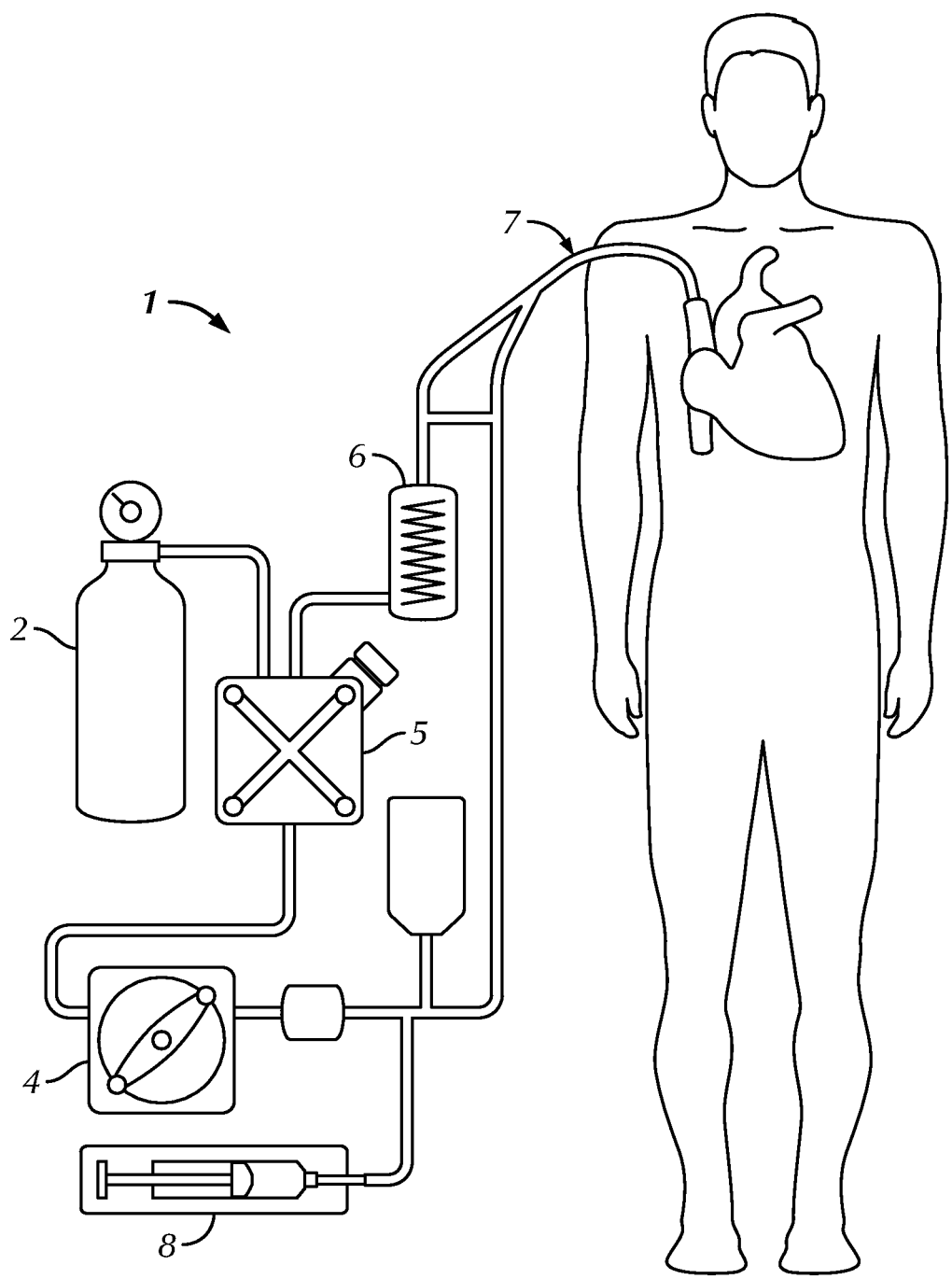
FIG. 1 is a schematic diagram of a prior art extracorporeal membrane oxygenation system connected to a patient.

Certain terminology is used in the following description for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the geometric center or orientation of the system, device and instruments and related parts thereof. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 3-7, a readily transportable extracorporeal system, generally designated 100, 100', 100", for lung assist of a patient is preferably configured to include components for the operation of the transportable extracorporeal system 100, 100', 100" that preferably oxygenates the patient's blood, removes $CO_2$ and provides ventilation in a portable framework. The extracorporeal systems 100, 100', 100" in accordance with first, second and third preferred embodiments are shown in FIGS. 3-7 with the same reference numerals utilized to identify similar or the same features and a prime symbol (') utilized to distinguish the features of the second preferred embodiment of the system 100', as well as a double prime symbol (") utilized to distinguish the features of the third preferred embodiment of the system 100". The systems 100, 100', 100" preferably include an oxygen source or oxygen generating device 13 that is powered by a power source, preferably a battery 23, that is removable, replaceable and rechargeable to facilitate the transportability of the systems 100, 100', 100". The systems 100, 100', 100" are preferably, fully integrated so that use and transport are simplified. The systems 100, 100', 100" are not limited to including the removable, replaceable and rechargeable battery 23 and may include alternative power sources including AC power supplies such as two hundred thirty volt (230 V), fifty Hertz (50 Hz), one hundred fifteen volt (115 V), sixty Hertz (60 Hz), alternative direct current ("DC") power sources such as a connection to an auxiliary power outlet in an automobile or other sources of power that facilitate functioning of the systems 100, 100', 100".

The preferred extracorporeal systems 100, 100', 100" for lung assist are relatively easy to transport by the patient and within the hospital from one department to another. Common destinations include radiology for computerized tomography or other specialized imaging, the cardiac catheterization lab, or the operating room ("OR"). The most common reason for these transports of the systems 100, 100', 100" with the patient is to perform imaging, such as computerized tomography ("CT") scanning or conventional angiography in a cardiac catheterization laboratory. This imaging often requires that the preferred systems 100, 100', 100" be moved to a different location with and relative to the patient. For example, the preferred systems 100, 100', 100" are preferably slidable toward and away from or positionable at different locations relative to the head or feet of the patient to remove the systems 100, 100', 100" from a line of sight of the imaging machinery while not disturbing connections of cannulas 20a, 20b to the patient or to the components of the systems 100, 100', 100" (See FIGS. 6, 6C and 6D). Echocardiographic or fluoroscopic imaging is preferred to verify the proper placement of the cannula 20a, 20b. Intra hospital transport can also be employed to shift the patient to an ECMO bed in the intensive care unit ("ICU") when the ECMO is initiated elsewhere, such as in the operating room, emergency room, catheterization lab or in a hospital ward or clinic.

Echocardiographic or fluoroscopic imaging is preferred to verify proper placement of the cannula 20a, 20b to increase the probability of successful functioning of the systems 100, 100', 100". Intra hospital transport can also be performed to shift the patient to the ECMO bed in the ICU when the ECMO is initiated somewhere else like in the OR, Emergency Room ("ER"), Catheterization Lab or in a Ward, such as for extracorporeal conventional cardiopulmonary resuscitation ("ECPR").

For vehicular and air transport, all equipment and components of the preferred systems 100, 100', 100" are able to maintain their proper function when subjected to extremes of temperature, vibration and other conditions that may occur during transportation or in-flight. Equipment of the systems 100, 100', 100" is also preferably able to pass electromagnetic interference ("EMI") testing so that its use does not interfere with aircraft navigation and control.

Common transport problems for prior art systems include equipment malfunction, leakage disconnection or rupture of part of the circuit, inadequate oxygen, flow issues & bleeding from the cannulation site. This illustrates the preference of utilizing the preferred systems 100, 100', 100" that include fewer external hoses and wires that can be tangled in the very crowded transport environment. Other inherent problems with transports for prior art systems include delays involved from the time of the initial referral until the arrival of the ECMO team, shortage of personnel, and human error. Any delay that occurs during transport can lead to adverse events.

Each of the above are industry concerns and it would be desirable design, develop and deploy smaller and portable controllers, pumps, and oxygenators, which is accomplished by the preferred systems 100, 100', 100".

In preferred embodiments, the systems 100, 100', 100" are portable dual membrane systems that remove $CO_2$ with a sub atmospheric pressure air sweep gas utilizing a $CO_2$/oxygenator 11 and an oxygen generating device or pressure swing adsorption ("PSA") module 13 that uses oxygen to oxygenate the blood after removal of the $CO_2$. The blood flow is in series, generally through an inlet cannula 20b, through a pump 10, through the $CO_2$/oxygenator 11 and back into the patient through an outlet cannula 20a. The gas or air flow in the preferred systems 100, 100', 100" is preferably through the $CO_2$/oxygenator 11 (may be vacuum driven), through a compressor 12, through the oxygen generating device or PSA module 13 where the $O_2$ is recycled after removing remaining $CO_2$ (if necessary) and nitrogen and argon if desired or necessary and back into the $CO_2$/oxygenator 11. The $CO_2$/oxygenator or PSA module 11 preferably includes a plurality of hollow gas permeable fibers in a first membrane 19a that are configured to permit diffusion of gas between the patient's blood that flows through the $CO_2$/oxygenator module 11 or between the blood flow inlet through the inlet cannula 20b and the blood flow outlet through the outlet cannula 20a. The blood from the patient that flows through the interior of the $CO_2$/oxygenator module 11 preferably flows past and through the gas permeable fibers to permit diffusion of gas between the patient's blood and the concentrated oxygen. The plurality of gas permeable fibers in the first membrane 19a are preferably positioned between the blood flow inlet of the inlet cannula 20b and blood flow outlet in the outlet cannula 20a such that blood flows around the plurality of hollow gas permeable fibers in the first membrane 19a. The plurality of hollow gas permeable fibers in the first membrane 19a preferably extend generally perpendicular to a direction of bulk flow of blood through the $CO_2$/oxygenator module 11. The plurality of hollow gas permeable fibers of the first membrane 19a are comprised of a gas transfer membrane.

In the preferred embodiments, the compressor 12 is comprised of a second moving element for moving gases, fluids and vapors in the systems 100, 100', 100". The second moving element or compressor 12 has an intake port at an inlet side and an outtake port at an outlet side. The compressor 12 is connected to a hollow transport conduit 42. The hollow transport conduit 42 includes a proximal opening 42a and a distal opening 42b. The proximal opening 42a is in fluid connection with the outtake port of the of the second moving element or the compressor 12.

The levels of concentration of $CO_2$ and/or $O_2$ in the patient's blood can be checked by "looking" at the blood, collecting data from sensors 22, 30 regarding the blood or sensing the $CO_2$ or $O_2$ concentration in the blood with an optical or other sensor 22. The sensor 22 may be positioned at or near the $CO_2$/oxygenator membrane 11, preferably near an air inlet. The sensor 22 may be comprised of a sensor that measures or senses $CO_2$ or $O_2$ in the gas flow via fluorescence or quenching, which uses a bifurcated optical fiber that has a light source sending and photo receiving unit on one end and is coated with a Ruthenium compound on the other end. This sensing is generally non-contact and reacts to changing $CO_2$ levels or $O_2$ levels, is relatively small and utilizes minimal power. The sensor 22 of the systems 100, 100', 100" may be comprised of a fluorescence or quenching sensor that is in communication with a central processor 28, which may utilize the $CO_2$ concentration or $O_2$ concentration collected data to drive operation of the preferred systems 100, 100', 100". The sensor 22 is not limited to the above-described sensors and may be comprised of any sensor that is able to sense or measure $CO_2$ and/or $O_2$ concentrators or nearly any other property of the blood that flows through the systems 100, 100', 100" and that may facilitate operation of the systems 100, 100', 100". The sensor 22, for example, may be comprised of an optical or optode sensor 22 that is able to optically measure a substance, such as oxygen or $CO_2$, typically with the aid of a chemical transducer. The central processor 28 may also be in communication with other oxygen and $CO_2$ sensors 30 that are otherwise positioned in the airflow or blood flow of the systems 100, 100', 100", such as in the $CO_2$/oxygenator module 11 or the oxygen generating device 13, in the inlet or outlet cannulas 20b, 20a. The central processor 28 is also preferably in communication with and is able to open and close the valves 17, as well as operate the first moving element or pump 10 and the second moving element or the compressor 12.

A more simplified version of the preferred systems 100, 100', 100" may utilize a single membrane that performs both functions of $CO_2$ removal and some oxygenation or that combines the operation and functions of the $CO_2$/oxygenator module 11 and the oxygen generating device 13. The preferred systems 100, 100', 100" provide oxygen with the on-board pressure swing adsorption system 13 that is essentially a portable oxygen concentrator with extra gas purification capabilities.

ECMO systems, even of the low flow $ECCO_2R$ type, require large amounts, such as four to eight liters per minute (4-8 L/m) of oxygen for sweep gas and oxygen supply. This would require a large concentrator that could have a weight of approximately thirty-five pounds (35 lbs) and more power than a battery can reasonably supply in a portable machine. Thus, it becomes preferable to recycle the oxygen after it exits the second membrane or pressure swing adsorption device 13 in the preferred systems 100, 100', 100". The exit gas is still mostly oxygen and only contains about fifty milliliters/minute (50 ml/min) of $CO_2$. The pressure swing adsorption system 13 is designed to use this exit gas as the input to the PSA compressor 12 and the adsorbents in the system are preferably selected to be able to remove $CO_2$, Argon, and nitrogen from the gas stream. In order to produce a flow of four liters per minute (4 L/min) of oxygen it is only necessary to provide 'makeup' oxygen in the amount of about one liter per minute (1 L/min). This reduces the power requirement to about forty-five Watts (45 W) and preferably reduces the mass of the PSA system 13 to about three pounds (3 lbs.).

Figure 3:
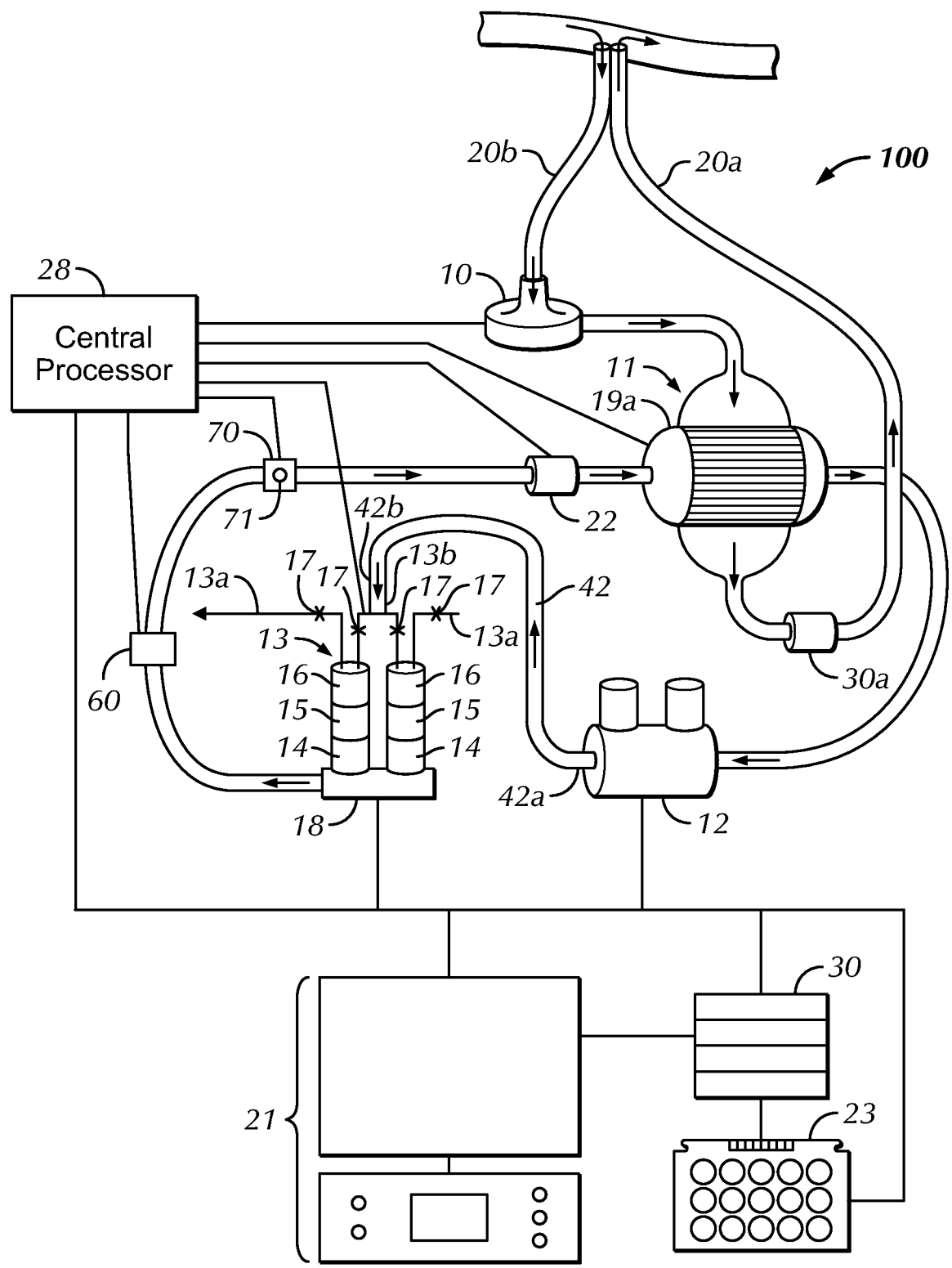
FIG. 3 is a schematic diagram of a portable extracorporeal system for lung assist in accordance with a first preferred embodiment of the present invention.
Figure 4:
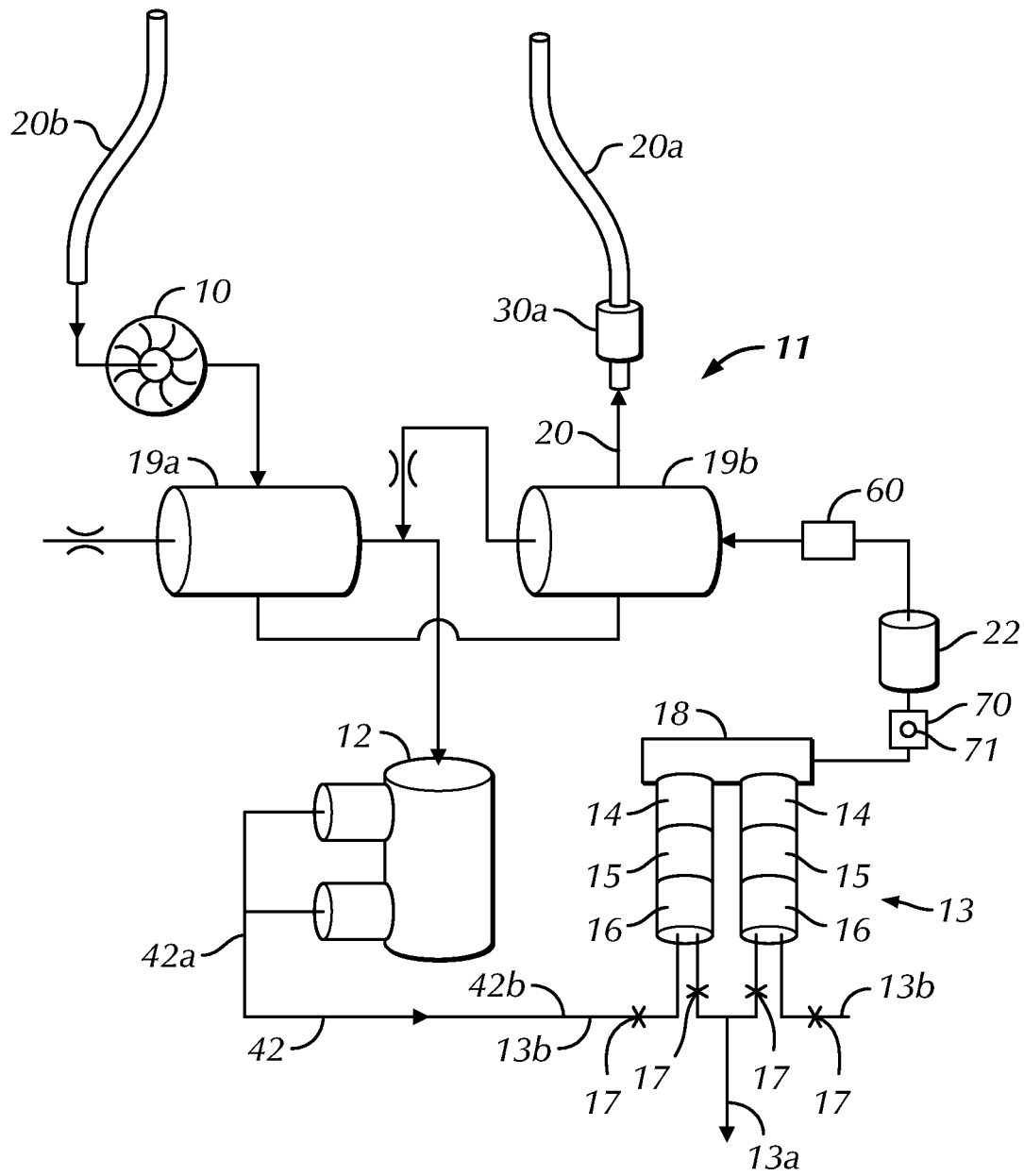
FIG. 4 is a schematic diagram of an alternative portion of the system of FIG. 3.
Figure 4A:
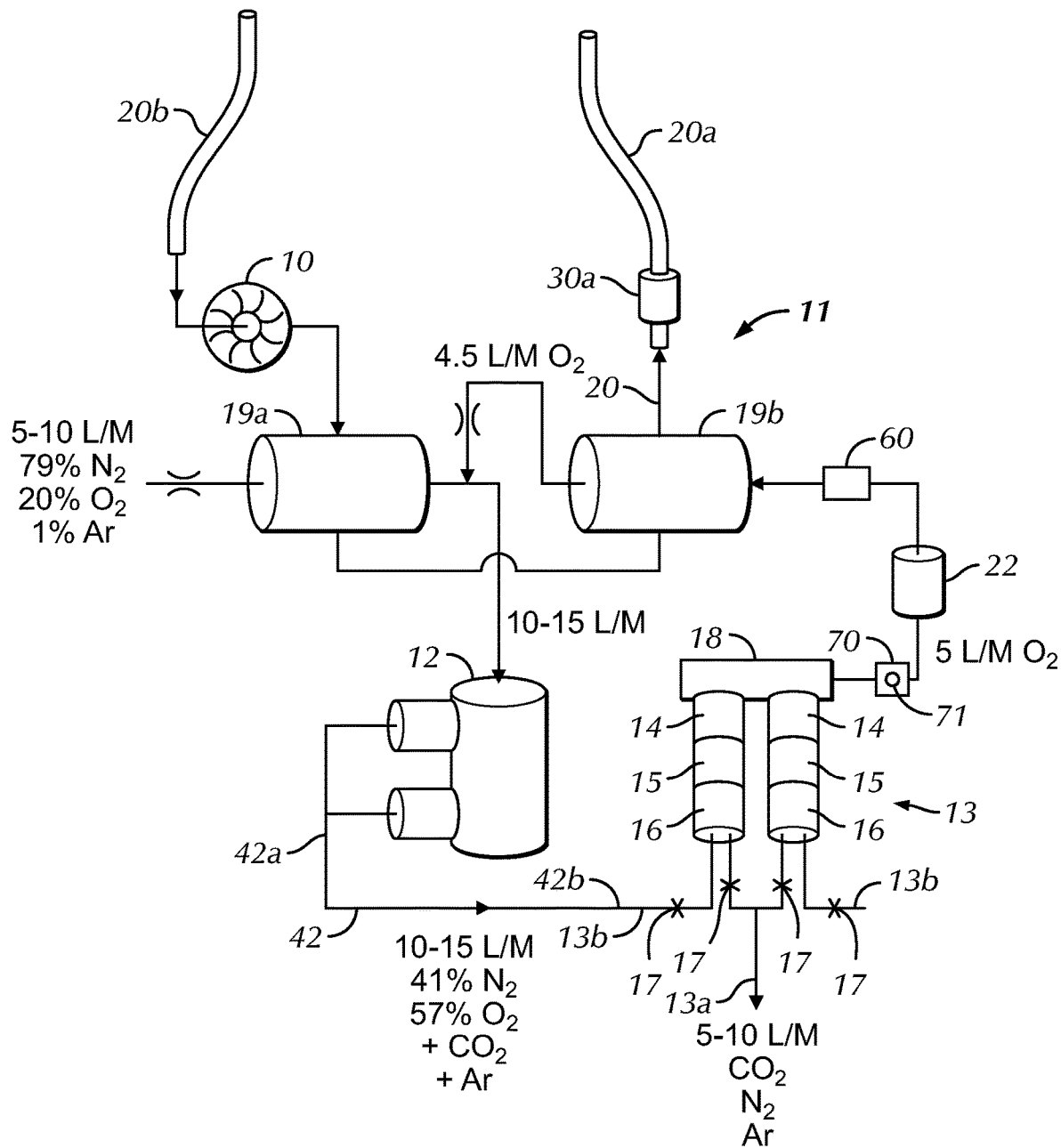
FIG. 4A is a schematic diagram of the alternative portion of the system of FIG. 4.

The internal components and features of the preferred systems 100, 100', 100" are described with references to FIGS. 3-4A and the components of the systems 100, 100', 100" are preferably housed within a housing 40', 40".

Figure 3A:
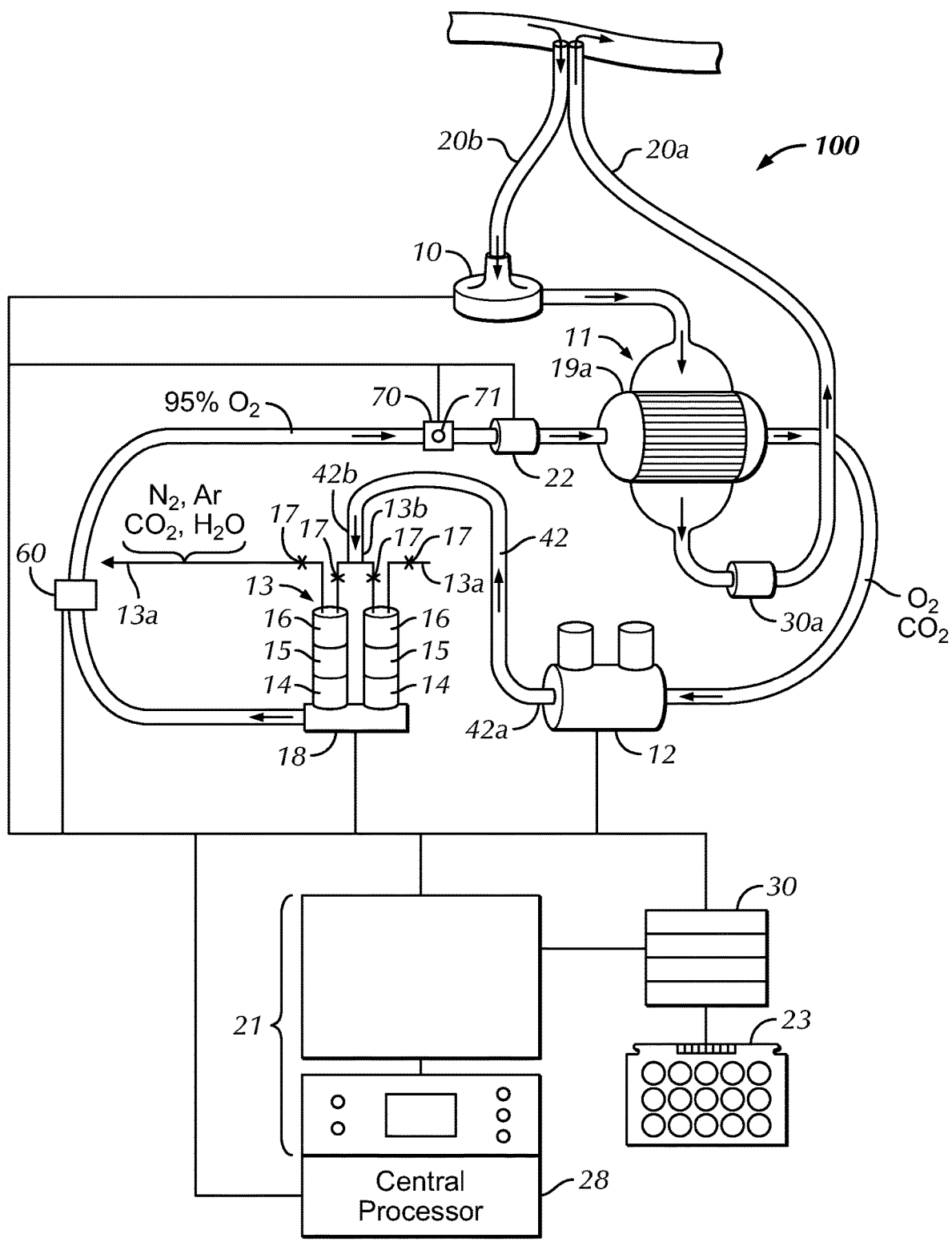
FIG. 3A is an alternative schematic diagram of the system of FIG. 3.

Referring to FIGS. 3 and 3A in the single membrane system of the first preferred embodiment, venous blood enters the pump 10 through the inlet cannula 20b and is pumped to the $CO_2$/oxygenator module 11. The compressor 12 pulls oxygen from the gas side of the $CO_2$/oxygenator module 11 and delivers it along with a small quantity of makeup air to a second membrane, PSA module or oxygen generating device 13 where adsorbents 14, 15, 16 within the oxygen generating device 13 preferably remove argon, carbon dioxide, and nitrogen along with some water vapor. The oxygen generating device 13 is not limited to including the argon removing adsorbent 14, the carbon dioxide removing adsorbent 15 and the nitrogen removing adsorbent 16 and may include only a single one of the adsorbents 14, 15, 16, pairs of the adsorbents 14, 15, 16 or additional adsorbents 14, 15, 16 that remove additional components of the air flowing through the oxygen generating device 13. The oxygen product gas is returned to the $CO_2$/oxygenator module 11 via a product manifold 18 and through the sensor 22, which may be comprised of an optical sensor. The adsorbents 14, 15, 16 are preferably specialized to remove particular gases, for instance argon may be removed with a silver exchanged zeolite adsorbent or a first adsorbent 14, nitrogen could be removed with a lithium exchanged zeolite adsorbent or a second adsorbent 15 and $CO_2$ could be removed with a 5A-type zeolite adsorbent or a third adsorbent 16. The preferred silver exchange zeolite adsorbent or argon removing adsorbent 14, lithium exchanged zeolite adsorbent or carbon dioxide removing adsorbent 15 and the 5A-type zeolite adsorbent or nitrogen removing adsorbent 16 are not limiting and the first, second and third adsorbents 14, 15, 16 may be comprised of other materials and adsorbents to target specific materials, preferably gases, for removal from the medium, preferably air, flowing past the adsorbents 14, 15, 16 in the $CO_2$/oxygenator module 11. Special use of multiple adsorbents 14, 15, 16, a technician replaceable oxygen generating device 13, and flow controls that regulate gas flows with a central processor 28 allow a one liter per minute (1 L/min) system to take the place of a four or five liter (4 L/min or 5 L/min) system allowing portability and low power usage.

Referring to FIGS. 4 and 4A, the first preferred extracorporeal system 100 may operate with dual membranes 19a, 19b in the $CO_2$/oxygenator module 11 (FIGS. 4 and 4A) or may operate with a single membrane 19a (FIGS. 3 and 3A). In the first preferred system 100 the blood enters the pump 10 from a venous lumen or the inlet cannula 20b and is pumped through the $CO_2$/oxygenator module 11 where carbon dioxide from the blood permeates into the negative pressure air supply that is generated by an inlet of the compressor 12. Air and a relatively small quantity of carbon dioxide, such as approximately thirty to seventy milliliters per minute (30-70 ml/min), is preferably mixed with the outlet gas from a first membrane 19a, which is comprised mostly of oxygen, and is compressed and sent to the pressure swing adsorption ("PSA") module 13. The composition of the compressor outlet gas is, for example, about one half air and one half oxygen or forty percent (40%) nitrogen, one-half percent (0.5%) Argon, seventy-five hundredths percent (0.75%) carbon dioxide, and fifty-eight and seventy five hundredths percent (58.75%) oxygen. The PSA module 13 preferably contains a plurality of adsorbents 14, 15, 16 that remove significant portions of the nitrogen, carbon dioxide, argon and water vapor that may be in the gas stream. The PSA module 13 acts continuously by being pressurized to adsorb and depressurized to desorb the unwanted gasses. This process is preferably accomplished via valves 17 that are in communication with the adsorbents or adsorbent beds 14, 15, 16. The oxygen enriched product gas leaves the PSA module 13 via a product gas manifold 18 and goes to the $CO_2$/oxygenator module 11 with the first membrane 19a where the blood flow from the pump 10 is oxygenated. The blood then flows via the outlet cannula 12b to the patient. This arrangement produces a preferred level of carbon dioxide reduction and blood oxygenation using the relatively smallest equipment footprint and the least amount of power without requiring an external oxygen source.

The first preferred system 100 is preferably powered by a battery 23. The battery powered system 100 is preferably self-contained and preferably consumes less than sixty-five Watts (65 W) of power, such as a forty-five Watt (45 W) PSA module 13, a fifteen Watt (15 W) blood pump 10, and five Watt (5 W) electronics, preferably including a display 21, the sensor 22 and other sensors 30. In both iterations the PSA module 13 is preferably replaceable as a plug in unit so when the adsorbents or adsorbent beds 14, 15, 16 become contaminated or operate beyond their useful life a technician can replace PSA module 13 or the adsorbents 14, 15, 16. In addition, if certain blood gasses are preferably targeted for removal or oxygenation is more or less important, the adsorbents 14, 15, 16 can be tailored to that application and the PSA module 13 can be chosen from a catalog of PSA modules 13 that are pre-designed for the specific application.

Referring to FIGS. 3-4A, the first preferred advanced integrated extracorporeal system 100 incorporates features that make it suitable for a variety of treatment options without having to assemble and connect additional equipment.

The pump or first moving element 10 is utilized to create velocity fields in blood flow contacting the plurality of hollow gas permeable fibers in the oxygenator membranes 19a, 19b of the $CO_2$/oxygenator module 11.

The other sensors 30 may include a sensor that is located at an entrance or exit of the blood circuit as the blood flows through the CO2/oxygenator module 11 and/or at the inlet or exit of the gas circuit as the gas flows through the CO2/oxygenator module 11. Such positioning of the other sensors 30 allows the preferred systems 100, 100', 100" to respond to changing conditions of the gas and blood, particularly based on collecting the data at the central processor 28, the central processor 28 analyzing the collected data and the central processor 28 sending signals to the systems 100, 100', 100" to modify operation. If one of the other sensors 30 is a CO2 sensor located in the blood flow indicates that a predetermined sufficient amount or level of CO2 is being removed from the blood or achieved in the blood, then the central processor 28 may reduce the operating speed of the oxygen generating module 13 or ramp down the oxygen generating system 13, as less concentrated oxygen gas is needed to sweep CO2 out of the blood. This reduction in operating speed or ramp down of the oxygen generating device 13 reduces energy use and preserves power levels of the battery 23. In addition, the blood flow through the blood pump 10 could be reduced if the other sensors 30 sense a sufficient amount or level of CO2 is being removed from the blood during operation. If the other sensors 30 indicate that the CO2 amounts or levels are changing (more exit CO2 than entrance CO2 in the oxygenator module 11) then the oxygen generating device or PSA module 13 may be adjusted, preferably based on a signal from the central processor 28, to produce the optimal change in CO2 level or amount for the blood flow and energy input to the PSA module 13.

In the preferred embodiment, the central processor 28 includes an algorithm based on clinical data to determine the optimal CO2 reduction rate for a given condition (disease) vs time under treatment. Other data that may also be collected by the central processor 28 via the other sensors 30, such as body temp with a thermometer, respiration rate via a pressure sensor, blood chemistry via a blood chemistry sensor, heart rate via a heart rate monitor, and related physiological data of the patient can be used as inputs to the central processor 28 for the algorithm, which is preferably calculated by the central processor 28. The response to the algorithm, such as a preference to change blood flow, change gas chemistry, and related preferred patient outcomes, can be based on patient personal data and or historical disease progress data that is also input to the central processor 28. Inflection points may be derived by the central processor 28 that address treatment options such as changing medication being dispensed to the patient, transitioning the patient from intubation to non-invasive ventilation, changing O2 or CO2 levels in breathing gas delivered to the patent, and related transitions and modifications to the operation of the systems 100, 100', 100" relative to the patient. Further, excess O2 may be redistributed in certain clinical situation to the ventilation module 38', 38", the concentrated oxygen reservoir 60, the concerver 66 or $CO_2$/oxygenator module 11 to preferably maximize healing of the patient.

Figure 5:
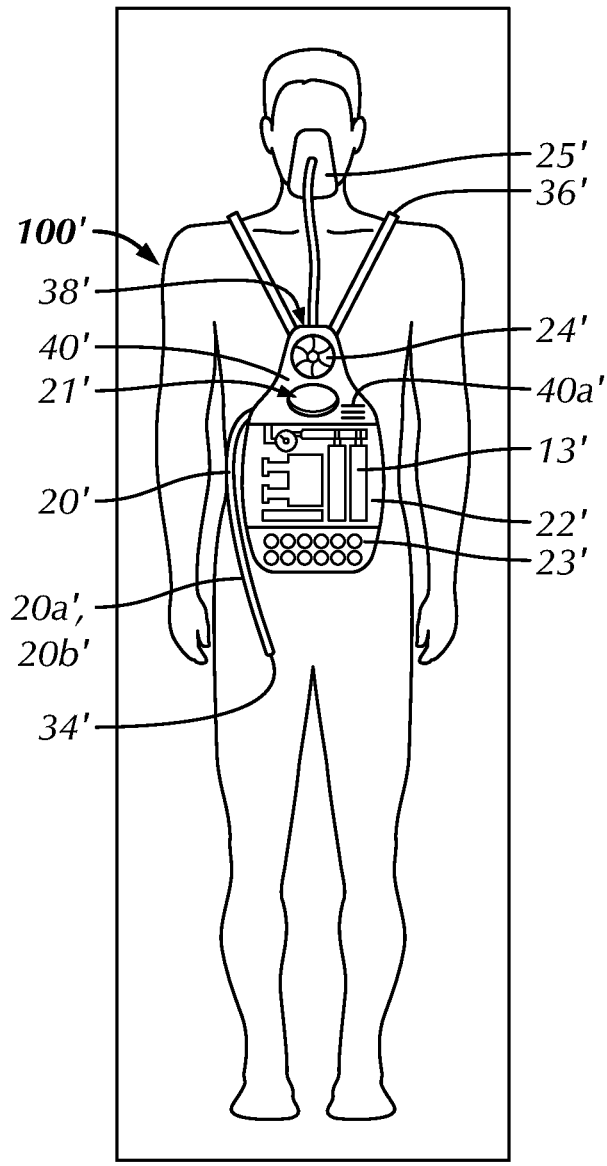
FIG. 5 is a top plan view of a portable extracorporeal system for lung assist in accordance with a second preferred embodiment of the present invention, wherein the system is portable and selectively mountable to a patient.
Figure 5A:
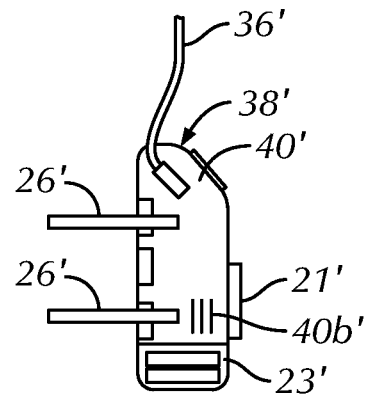
FIG. 5A is a side elevational view of the extracorporeal system of FIG. 5.
Figure 5B:
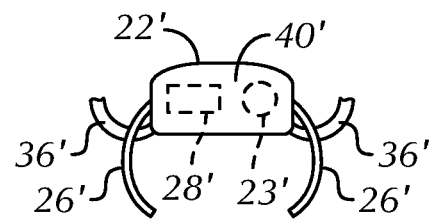
FIG. 5B is a front elevational view of the extracorporeal system of FIG. 5.

Referring to FIGS. 5-5B, in a second preferred embodiment, the portable extracorporeal system 100' includes substantially the same or similar components to the first preferred portable extracorporeal system 100, but is arranged and positioned within the housing 40' to consolidate the components and substantially enclose the system 100'. The preferred housing 40' generally encloses and protects the components of the system 100' except for arms 26', which are described in greater detail below, the dual lumen cannula 20', which extends from the housing 40' to an insertion site 34' in the patient and a mask 25' and associated tubing that may provide positive pressure air or concentrated oxygen to the patient. The housing 40' is positionable at various locations relative to the patient to facilitate conducting procedures on the patient while the system 100' is operational or to move the system 100' out of the way of medical personnel who are performing the procedure on the patient.

Referring to FIGS. 3-5B, the second preferred portable extracorporeal system 100', as illustrated in FIGS. 5-5B, is wearable with a shoulder harness and/or a belt type fastening system 36'. A blower 24' is preferably integrated into the system 100' to provide continuous positive airway pressure to the patient. The blower 24' is connected by a hose 24a' to a mask 25' (FIG. 5). The operating speed of the blower 24' is adjustable either by a manual control setting or an electronic control that reacts to patient physiologic conditions based on collected data from the sensors 22, 30 that are in communication with the central processor 28'. Internal batteries 23a' preferably provide extra operating time in the event of external battery 23' failure or discharge and to provide constant operation during removal and replacement of the external battery 23'. The external battery 23' is preferably removable, replaceable and rechargeable to facilitate the transportability of the system 100'.

The dual lumen cannula 20' preferably connects the 'wet side' pump/membrane 10 to a venovenous insertion site 34' in the patient. The insertion site 34' is preferably proximate an inlet cannula inlet where blood from the patient enters the inlet cannula 20b. The inlet cannula 20b is comprised of a blood flow inlet where blood from the patient is drawn and enters the housing 40' under a drawing pressure created by the pump 10'. The dual lumen cannula 20' and the inlet cannula 20b are in fluid connection with the housing 40', specifically with the pump 10' within the housing 40'. A blood flow outlet is comprised of the outlet cannula 20a, which is in fluid connection with the housing 40'. The outlet cannula 20a extends from the outlet of the $CO_2$/oxygenator module 11, out of the housing 40', through the insertion site 34' and back into the patient's vessel to introduce oxygenated blood into the patient's vessel. The outlet cannula 20a is in fluid communication with the housing 40', specifically the outlet of the $CO_2$/oxygenator module 11.

Electronics and a display 32' preferably show device and patient condition data collected from the sensors 22, 30 and stored and/or analyzed by the central processor 28'. Arms 26' (See FIGS. 5-5B) elevate the device above the patient to reduce pressure on the abdomen or other portions of the patient's body and to allow repositioning during imaging procedures where the second preferred system 100' may need to be moved toward the head or feet while still maintaining undisturbed connection of the cannula 20' at the insertion site 34' and positioning of the mask 25' on the patient's face. The system 100' can also be mounted on a roll around stand or table if preferred, without significantly impacting the design, operation and configuration of the second preferred system 100'. FIG. 5 shows how the system 100' is placed on the patient with the shoulder harness and belt fastening system 36' and the arms 26', but the system 100' may otherwise be placed on the patient, the patient's bed or on a cart next to the patient's bed.

Various system and patient data can be collected during operation of the systems 100, 100', 100", such as heart beat, breathing rate, blood oxygen, body temperature, pressures, flow rates and related data that may be collected by the sensors 22, 30. The sensors 22, 30 can be built into the systems 100, 100', 100", such as within the housing 40', and monitored on the display 21' by a user, technician, physician or other personnel. The central processor 28, 28' preferably provides control of at least the oxygen generating device or PSA module 13, 13', blood pump 10, and ventilation blower 24' functions and inputs the various sensor readings from the sensors 22, 30. Sensor readings and collected data from the sensors 22, 30 are compared to alarm setpoints in the central processor 28, 28' to alert for low flow, high back pressure, low battery, low oxygen, compressor failure, and other biometric and equipment housekeeping parameters that may be monitored by the system 100, 100' and analyzed by the central processor 28, 28', preferably based on setpoints stored in the central processor 28, 28'.

Figure 2:
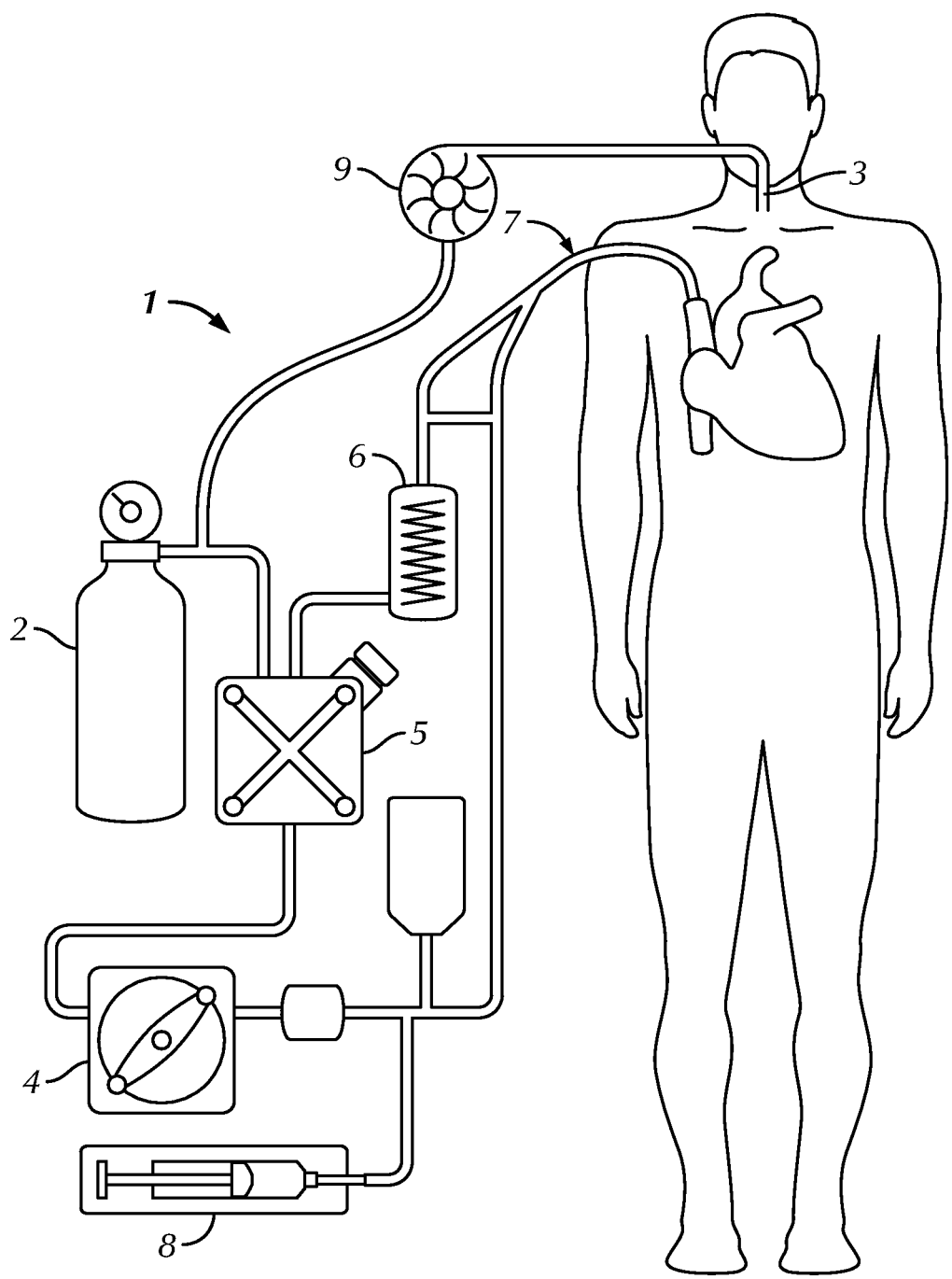
FIG. 2 is a schematic diagram of a prior art extracorporeal membrane oxygenation system with a respiration component connected to a patient.

Referring to FIGS. 1 and 2, a prior art system 1 includes a pump, an oxygenator, support for cardiac and/or pulmonary function, a large, complex system, requires specialist team and facility, requires cart with bottled oxygen 2 or connection to wall oxygen, very costly, high flow rates, such as one to six liters per minute (1-6 L/min), large cannula/catheter bore, high incidence of adverse events and life support, which are difficulties or limitations of the prior art system of FIGS. 1 and 2.

Referring to FIGS. 3-6D, the preferred systems 100, 100', 100" include the pump 10 and $CO_2$/oxygenator module 11, supports partial cardiac and/or pulmonary function, is operational for days to weeks, extended use outside the OR, addresses conditions such as acute respiratory distress syndrome ("ARDS"), Influenza, Pneumonia, H1N1, SARS, MERS, as well as related treatment strategy, veno-venous operation, low flow, such as four tenths to one liter per minute (0.4-1.0 L/min), relatively small cannulas 20, reduced risk of adverse events, generally not life support, smaller, less complex device, relatively inexpensive, ambulatory and transport-friendly, self-contained $O_2$ supply, typically no $CO_2$ canister, $CO_2$ removal increases $O_2$ uptake and the possibility to eliminate all $CO_2$ at approximately one-half liter per minute (0.5 L/min) flow.

Referring to FIG. 2, a tube 3 is placed in a patient's trachea that supports respiration for days to weeks, extended use to assist lung function, mechanical ventilator veno-arterial, and potentially results in complications for the patient such as being invasive, especially for older patients, patient cannot speak or eat, high risk of ventilator acquired pneumonia and initiating and exacerbation of lung damage.

Figure 6:
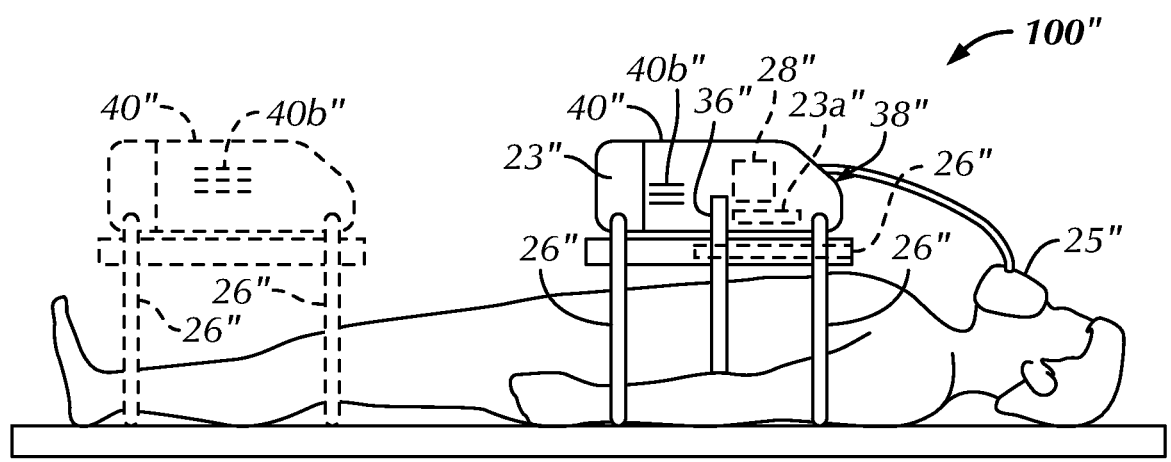
FIG. 6 is a side elevational view of a portable extracorporeal system for lung assist in accordance with a third preferred embodiment of the present invention, wherein the system is positioned relative to the patient in two different placements with a second lower placement shown in dashed line type and, particularly showing preferred arms that are able to space the system from the patient to reduce pressure on the patient during use and various placements of the system relative to the patient utilizing the arms or support structure.
Figure 6A:
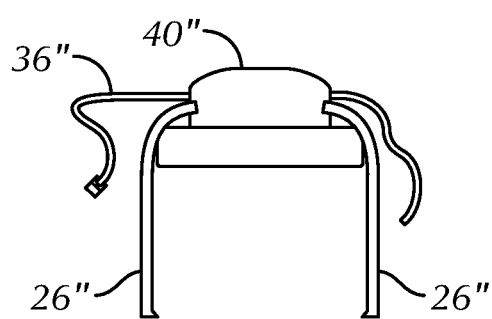
FIG. 6A is front elevational view of the extracorporeal system of FIG. 6
Figure 6B:
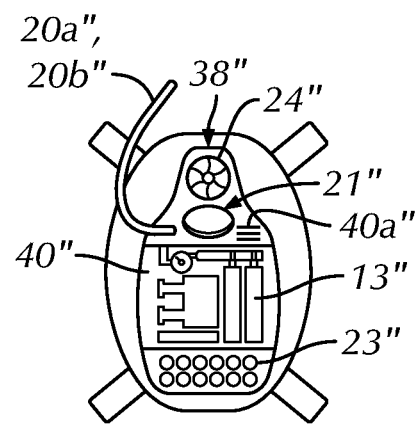
FIG. 6B is a top plan view of the extracorporeal system of FIG. 6.
Figure 6C:
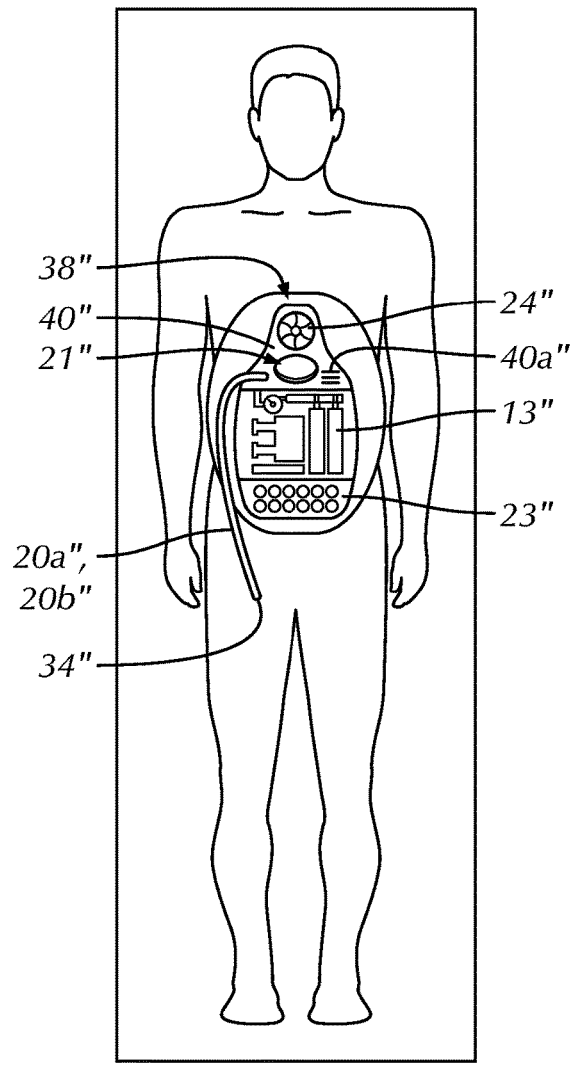
FIG. 6C is a top plan view of the extracorporeal system of FIG. 6, wherein the system is positioned proximate the patient's chest.

Referring to FIGS. 3, 5 and 6, the second and third preferred systems 100', 100" include a ventilation module 38', 38" comprised of at least the blower 24', 24" and mask 25', 25", which assist breathing for days to weeks, extends use outside the OR, improves lung function and quality of life, is generally non-invasive, results in fewer adverse events and complications, is easy to administer in a general ward, is an accepted treatment for hypercapnia, increases the likelihood of the patient being able to eat and talk, is adaptable for use with protective flow settings that can be used when treatment is combined with $ECCO_2$-R and increases mobility. For patients temporarily receiving ECMO or $ECCO_2R$ treatment, successfully weaning the patient off of ECMO or $ECCO_2R$ generally improves with the ventilation module 38', 38". The housing 40', 40" also preferably includes a display 21', 21" proximate the blower 24', 24" to display collected data and other related information controlled by the central processor 28.

The ventilation module 38', 38" may be comprised of the adjustable blower 24', 24" and mask 25', 25", but is not so limited and may be comprised of a more complex ventilator comprising, but not limited to, a pressure generator, a gas blender, a gas accumulator, an inspiratory flow regulator, humidification equipment, an expiratory regulatory, gas tubing, intake filters, moisture traps, bacteria filters and various sensors for measuring gas concentration, flow pressure, volume and related operational parameters of the ventilation module 38', 38". The ventilation module 38', 38" may further include a gas, flow and pressure regulator that can adjust the volume, flow rate, concentration and pressure of oxygen or oxygen and nitrogen gas mixture that is delivered to mask 25', 25". The preferred regulator includes a mechanical or electro-mechanical mechanism that is configured for adjusting oxygen mixtures for delivery to the patient. The preferred mask 25', 25" may be comprised of a nasal cannula, facially sealed mask, bi-Pap mask, or other similar interfaces such as the Breathe Pillow Interface® sold by Breathe Technologies (Irvine, Calif.). The preferred systems 100', 100" may be configured to deliver concentrated oxygen from the PSA module 13 to the patient through the ventilation module 38', 38".

The preferred systems 100, 100', 100" combine these two Low Flow $ECCO_2R$/ECMO and non-invasive positive pressure ventilation designs into a single transportable package in the housing 40', 40" that is relatively easy to move with the patient, can be placed on a nearby pole or table, can be attached to the patient for ambulation or wheelchair transport, can be repositioned for imagining and other in hospital procedures (See FIGS. 6, 6C and 6D), and is preferably entirely self-contained. The preferred systems 100, 100', 100" include the $CO_2$/oxygenator module 11 and the oxygen generation device or pressure swing adsorption module 13. The arrangement of components preferably results in the systems 100, 100', 100" being easily adaptable to changing treatment environments, and eliminates numerous hoses, wires, attachments (excepting cannula and breathing tube) that are extraneous to the operation of the systems 100, 100', 100". The components of the third preferred embodiment are preferably powered by a removable, rechargeable and replaceable battery 23".

ECMO, $ECCO_2R$, and ECLS are terms that are sometimes used interchangeably because they share common components, but have different applications separated by degrees of invasiveness and degrees of life support. The design of the preferred systems 100, 100', 100" is more of a life assist device or extracorporeal life assist ("ECLA") device or system for situations where, for example, a patient has partial lung capacity such as from an acute respiratory distress event or illness such as H1N1, SARS, MERS, coronavirus or pneumonia, although the preferred systems 100, 100', 100" could also be used for life support for relatively short periods of time. The preferred systems 100, 100', 100" provide portable, less expensive treatment when compared to ECMO and $ECCO_2R$ systems that are replacements for large ECMO/$ECCO_2R$ systems in hospitals today. The preferred systems 100, 100', 100" may be incorporated into infusion or dialysis clinics or other non-emergency care centers in relatively large numbers at a comparatively lower cost to provide this service and treatment for patients in these environments.

A study titled "Extracorporeal Membrane Oxygenation for Severe Acute Respiratory Distress Syndrome" from the New England Journal of Medicine on May 24, 2018 reported that thirty-five percent (35%) of the ECMO group and forty-six percent (46%) of the control group died. The study was halted because the clinicians believed there was no statistical difference between the ARDS patient's that received ECMO and the control group that received standard ventilator treatment. The clinicians, however, apparently underappreciated the approximately twenty-four percent (24%) fewer patient deaths in the ECMO group. Moreover, that does not include the cross-over population. Thirty-five (35) of one hundred twenty-five (125) in the control group or twenty-eight percent (28%) were performing so poorly on the ventilator in the control group that they were crossed over to the ECMO where forty-three percent (43%) survived. This is an important clinical factor that has been overlooked.

A study in the early 1980's related to ECCOR found that low-flow, or partial, $ECCO_2R$ (also referred to in the literature as DECOR) by Gattinoni et al. and published in 1986 (JAMA, 256:7, 881-886) showed that if extracorporeal support was used to provide removal of only thirty-three percent (33%) of estimated basal $CO_2$ production in patients maintained with noninvasive ventilatory support, significant drops in tidal volume could be achieved with relatively small decreases in partial pressure of carbon dioxide ("$PaCO_2$").

The equipment utilized by Gattinoni, and others today, however, are not mobile or otherwise portable. Nor is the ventilator, oxygen source 2, sweep gas, oxygenator and associated pump of the prior art system 1 integrated into a single system that can adjust blood oxygen levels by simultaneously adjusting one or more of the following: (1) oxygen flow or volume into the oxygen membrane; (2) rate of carbon dioxide removal; (3) concentration level of the oxygen into the membrane; (4) volume and flow of air through the ventilator fans; (5) volume and flow of oxygen from the oxygen generating source; and (6) concentration of oxygen into the ventilated air delivery mechanism.

Such factors can be adjusted manually in response to data collected on blood oxygen and blood $CO_2$ levels, but in the preferred embodiments of the systems 100, 100', 100", such adjustments may be made automatically by the central processor 28. For example, a valve can be connected to the cannula 20 that permits periodic removal of blood to test for $CO_2$ levels using the sensors 22, 30. A simple disposable cartridge or syringe could be attached to draw blood for testing.

Blood oxygen concentration levels could be derived from the same sample or from a pulse oximeter or one of the other sensors 30 that may be applied on the patient. The other sensors or plurality of sensor 30 are preferably in communication with the central processor 28 and may be comprised of a battery sensor, a pressure sensor, a flow sensor, an oxygen concentration sensor, an oxygen sensor, a global positioning system ("GPS") tracking, an operation time sensor or other related sensors that may collect data regarding operation of the preferred systems 100, 100', 100". This information, along with activated clotting time ("ACT") testing for anti-coagulant drug requirements could all be delivered to the central processor 28, 28', 28" that then adjusts the above such factors. This is preferred particularly when the patient's lungs start to recover, and the patient needs to be weaned off the $ECCO_2R$ or ECMO.

During operation of ECMO, blood gas results and frequent measurements are key in the management of patients. Such results are important when weaning patients from ECMO. Current methods of blood gas analysis require arterial blood sampling from an appropriately located catheter or the circuit, which can only be undertaken intermittently. These intermittent samplings may be delay important medical care responses to changes in the patient's physiological, have a significant turnaround time, as blood samples are transferred to a central analyzer, expose the health-care professionals to the patient's blood, and result in iatrogenic blood loss, particularly when the patient's blood is thinned for the treatment, thereby resulting in increased potential for hemorrhage. To address these concerns inherent to ECMO, the preferred systems 100, 100', 100" an inline blood gas monitoring sensor or blood gas analyzer 30a may be incorporated into the outlet cannula 20a or an outlet of the $CO_2$/oxygenator module 11 to monitor the composition of the blood flowing back into the patient. The inline blood gas monitoring sensor 30 may be comprised of the Proxima blood gas analyzer, developed by Sphere Medical (Cambridge UK), but is not so limited and may be comprised of nearly any blood gas analyzer that may be incorporated into the systems 100, 100', 100" for monitoring the patient's blood. The inline blood gas monitoring sensor or blood gas analyzer 30a preferably enables rapid and frequent delivery of blood gas results to the central processor 28 and, preferably, directly at a patient's bedside for monitoring by medical personnel, potentially at the display 21. This then aids early decision-making and ensures closer control of therapy, including ECMO. When a blood gas measurement is desired, blood is withdrawn from the patient directly into the preferred blood gas analyzer 30a without the need for a technician to take a sample, deliver the sample to a blood analyzing department or mechanism and report the results of the analysis to the medical personnel. Results from the blood gas analyzer 30a may be displayed at the patient's bedside on the display 21 within are relatively short amount of time, such as three minutes (3 min).

During ECMO treatments, the risk of infections developing are increased for a patient, particularly if ECMO is used in immunocompromised patients. Since frequent arterial blood sampling is necessary, a key aspect of infection prevention and control with such patients is the stringent management of their blood samples, particularly during collection and transportation for analysis. The preferred blood gas analyzer 30a that is incorporated into the outlet cannula 20a or the $CO_2$/oxygenator module 11 minimizes potential exposure of the patient's blood, preferably containing the patient's blood within the housing 40 during operation and sampling.

The preferred systems 100, 100', 100" are preferably patient-dedicated and closed system, wherein the sensor 22, which may be comprised of an $O_2$ or $CO_2$ sensor 22, and the blood gas analyzer 30a keep infection control simple and effective, while also minimizing the number of openings of the arterial line for sampling. This protects both the patient's blood from exposure to blood stream infections, as well as the caregiver by limiting exposure to blood borne pathogens during the course of routine patient care. Furthermore, by avoiding transfer of blood to a central blood gas analyzer, the sensor 22 and the blood gas analyzer 30a also reduce blood handling and, therefore, reduce risk of infection transmission. Additionally, as all blood is returned safely to the patient directly through the outlet cannula 20a, this avoids the need for waste management of potentially infected blood specimens and syringes.

The preferred systems 100, 100', 100" may also include access points or ports for medication delivery, blood withdrawal or blood transfusion that are incorporated into the dual lumen catheter 20. The preferred systems 100, 100', 100" may further include the heater or heat exchanger 6 that could be added to the circuit for warming the blood prior to deliver to the patient, preferably in the dual lumen catheter 20 or in the circuit between the pump 10 and the $CO_2$/oxygenator module 11.

As described previously, portability is a preference of the invention contained herein. Affordability along with ease of deployment is also a preferred aspect. In addition to being available for ARDS events, the preferred systems 100, 100', 100" envisions multiple units being stored for deployment during natural disasters, flu epidemics, gas attacks or toxic explosions and other events where large populations of people could face severe respiratory distress.

Portability includes not only the patient being mobile with the preferred systems 100, 100', 100", but also mobile in that a patient, patient's stretcher or patient's bed can be quickly moved down a corridor with the systems 100, 100', 100" travelling with the patient as a single unit.

Figure 6D:
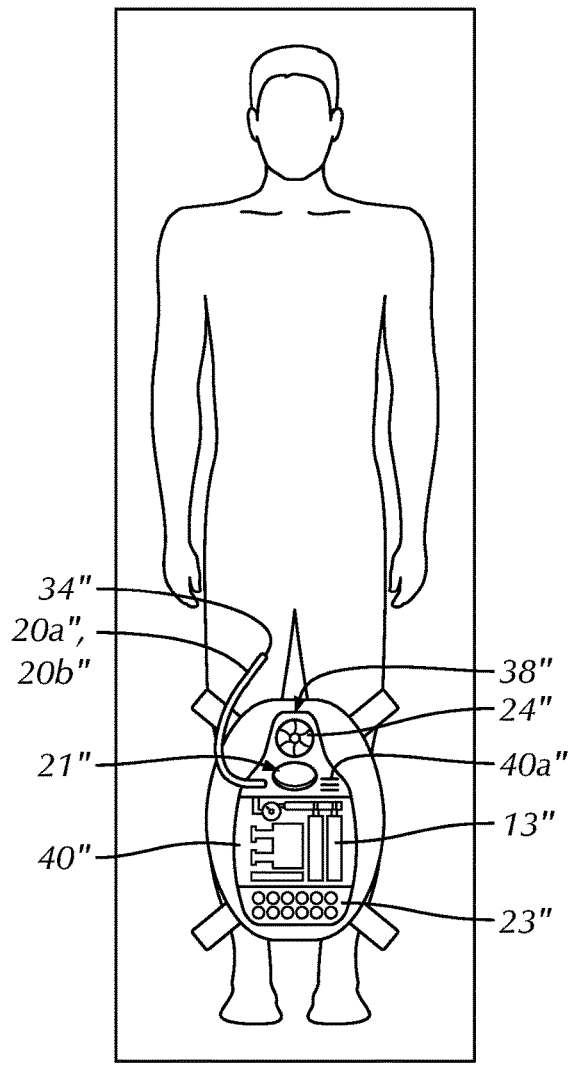
FIG. 6D is a top plan view of the extracorporeal system of FIG. 6, wherein the system is positioned proximate the patient's knees.
Figure 7:
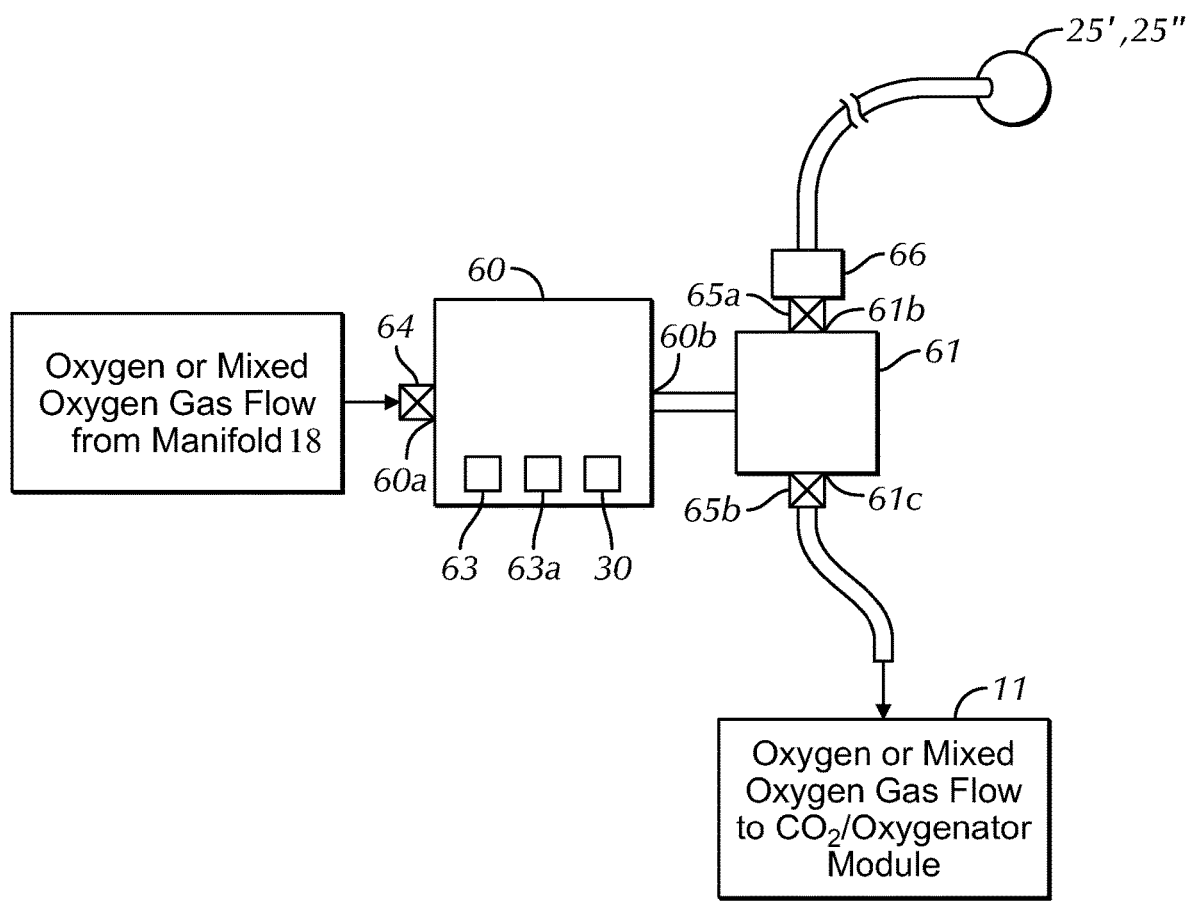
FIG. 7 is a block diagram of a module that may be utilized with any of the preferred embodiments of the extracorporeal system described herein.

Referring to FIGS. 6-6D, the third preferred system 100" includes the housing 40" with the arms 26" to position the system 100" relative to the patient. The arms 26" of the third preferred embodiment are pivotable from an extended position to a folded position. In the folded position, the arms 26" are pivoted to a position adjacent to the housing 40". The portability of the third preferred system 100" permits variable arrangement of the housing 40" relative to the patient to accommodate multiple medical procedures so that the housing 40" is out of the way and is able to maintain the positioning of the cannula 20" in the patient at the insertion site 34" with continued operation.

Referring to FIGS. 5-6D, the housing 40', 40" of the second and third preferred embodiments includes a gas inlet 40a', 40a" in fluid connection with the housing 40', 40" and in fluid connection with inlets of the plurality of hollow gas permeable fibers through the oxygen generating device module 13', 13". The housing 40', 40" also includes a gas outlet 40b', 40b" in fluid connection with the housing 40', 40" and outlets of the plurality of hollow gas permeable fibers through the oxygen generating device module 13', 13". The gas inlet 40a', 40a" facilitates introduction of ambient air into the system 100', 100" to produce concentrated oxygen in the oxygen generating device module 13', 13" and the gas outlet 40b', 40b" facilitates venting of the captured $CO_2$, argon, nitrogen and water out of the system 100', 100" during operation.

Referring to FIGS. 3-7, the concentrated oxygen generating device 13 is configured to generate concentrated oxygen from air that is preferably introduced to the oxygen generating device 13 through the gas inlet 40a', 40a" of the housing 40', 40". The oxygen generating device 13 includes a first outlet port 13a and a first inlet port 13b. The first outlet port 13a is in fluid connection with the gas inlet 40a and the first inlet port 13b is in fluid connection with the gas outlet 40b. The oxygen generating device 13 is configured to recycle waste oxygen from the gas transfer membrane or the oxygenator membrane 19 to increase throughput and remove, by an adsorption/desorption process, unwanted gasses. In the preferred embodiments, the concentrated oxygen generating device 13 includes the first adsorbent 14, the second adsorbent 15 and the third adsorbent 16 that facilitate removal of the unwanted gasses, which are comprised of carbon dioxide, argon and nitrogen. Each of the first, second and third adsorbents or sieve materials 13, 14, 15 is configured to target removal of one of the specific unwanted gasses for removal. The first, second and third adsorbents or sieve materials 14, 15, 16 may be contained within a sieve module or a plurality of sieve modules that include layers of zeolite material therein for adsorbing nitrogen, carbon dioxide and argon, as well as additional unwanted gasses that may preferably be removed from the product gas.

The sieve modules are preferably removable and replaceable from the oxygen generating device 13 to extend the useful life of the preferred systems 100, 100', 100" by replacing the sieve modules after the first, second, and third adsorbents or sieve materials 14, 15, 16 expire or exceed their useful life. The sieve modules may include first, second and third modules that incorporate, individually the first, second and third adsorbents or sieve materials 14, 15, 16 and the oxygen generating device 13 may include a plurality of sieve modules, such as two sieve modules, that each include the first, second and third adsorbent or sieve materials 14, 15, 16, but are not so limited. The oxygen generating device 13 may include sieve modules with only a single adsorbent material therein or a plurality of sieve modules with more than three adsorbent or sieve materials therein that target different gasses for removal from the product gas. In the preferred embodiment, the sieve modules are removable from and replaceable into the oxygen generating device 13 and the housing 40', 40" to replace sieve modules that exceed their useful life or begin to encounter degraded performance. The central processor 28 may monitor the operation of the oxygen generating device 13, such as by collecting data regarding the concentration of oxygen at the outlet of the oxygen generating device 13 to notify a use when the sieve modules should be replaced. 100, 100', 100"

The readily transportable extracorporeal system 100, 100', 100" may include a concentrated oxygen reservoir 60 that facilitates operation of the system 100, 100', 100" as a modular blood oxygenation ventilation system. The concentrated oxygen reservoir 60 is described herein in combination with the first preferred system 100, but may similarly be incorporated into any of the first, second and third preferred systems 100, 100', 100". The concentrated oxygen reservoir 60 is preferably located downstream of manifold 18 of the oxygen generating device or pressure swing adsorption module 13. The concentrated oxygen reservoir 60 is preferably designed to be resistant to moisture and capable of restraining oxygen or oxygen gas mixtures under various pressures that are utilized to facilitate gas flow to the first and second membranes 19a, 19b.

In operation, oxygen or mixed oxygen gas flows from the manifold 18 to the oxygen reservoir 60. At least one pressure sensor 63 is included in the concentrated oxygen reservoir 60 and is in communication with the central processor 28. The pressure sensor 63 is configured to monitor gas pressure inside the oxygen reservoir 60. An oxygen purity sensor 63a may also be incorporated into and located in the oxygen reservoir 60 to measure oxygen concentration. Both the oxygen purity sensor 63a and the pressure sensor 63 are configured to communicate with the central processor 28 and the central processor 28 is also preferably in communication with the concentrated oxygen reservoir 60 to control operation of the concentrated oxygen reservoir 60. A one way or controlled bi-direction valve 64 may be configured in the gas flow between the manifold 18 and the concentrated oxygen reservoir 60. The oxygen reservoir 60 preferably has an inlet port 60a and an exit port 60b. The one way or controlled bi-directional valve 64 is preferably secured to the oxygen reservoir 60 at or near the inlet port 60a to control flow of gas into the oxygen reservoir 60.

A reservoir manifold 61 is preferably mounted to the oxygen reservoir 60 at or near the exit port 60b of the oxygen reservoir 60. The reservoir manifold 61 of the preferred embodiments includes an inlet port 61a in fluid connection with the interior of reservoir 60 through the exit port 60b and an outlet port 61b, 61c. The preferred outlet port 61b, 61c includes first and second outlet ports 61b, 61c positioned at sides of the reservoir manifold 61 that splits the gas flow coming out of the exit port 60b of the oxygen reservoir 60.

The preferred systems 100, 100', 100" also include a reservoir valve 65b, 65c that is releasably connected to the outlet port 61b of the reservoir manifold 61. The preferred reservoir valve 65b, 65c is comprised of first and second reservoir valves 65b, 65c that are preferably releasably connected to the first and second outlet ports 61b, 61c, respectively. The first and second reservoir valves 65b, 65c are not limited to being releasably connected to the first and second outlet ports 61b, 61c and may be permanently secured to the first and second outlet ports 61b, 61c, may be otherwise mounted together or may be comprised of one outlet port 61b, 61c with one reservoir valve 65b, 65c. The first and second reservoir valves 65b, 65c are in communication with central processor 28 in the preferred embodiments. The central processor 28 preferably controls the flow of oxygen gas from the concentrated oxygen reservoir 60 through the reservoir valve 65a, 65b to the $CO_2$/oxygenator module 11. The central processor 28 also preferably controls the flow of oxygen gas from the concentrated oxygen reservoir 60 through the first and second reservoir valves 65a, 65b, which is then transmitted to the mask 25', 25". A conserver 66 may be located adjacent to valve 65b in order to sense patient inhalation or exhalation at mask 25'. A conserver 66 is arranged between the first reservoir valve 65a and the mask 25', 25" and communicates with central processor 28 to regulate the first reservoir valve 65a and the flow of purified oxygen to the patient, preferably through the mask 25', 25".

The first reservoir valve 65a and/or the conserver 66 may include an internal controller integrated therein that controls operation of the first reservoir valve 65a and/or the conserver 66 or may be in communication with the central processor 28 to facilitate updates or to convey collected data, but the local internal controller generally controls the first reservoir valve 65a and/or the conserver 66. The local or internal controller 67 preferably controls the flow of oxygen gas through first reservoir valve 65a instead of or in addition to the central processor 28. The internal or local controller preferably controls operation of the first reservoir valve 65a and/or the conserver 66 based on preset logic commands stored in the internal or local controller. In a non-limiting example, the internal or local controller may be comprised of a wearable Life2000 Ventilation System by Breathe Technologies, although the internal or local controller is not so limited and may be comprised of nearly any controller that may be incorporated into the systems 100, 100', 100" to control the operation of the first reservoir valve 65a and/or the conserver 66.

For initial patients suffering from an acute respiratory event where mechanical ventilation is generally insufficient to relieve the patient or risks severe damage to the patient's lungs, the preferred systems 100, 100', 100" described herein generally allow such patient to receive blood oxygenation and $CO_2$ removal via the CO2/oxygenator module 11 with the first and/or second membranes 19a and 19b, while also receiving concentrated oxygen from the concentrated oxygen reservoir 60 through the mask 25', 25" at relatively low levels. As the patient recovers, blood oxygenation and $CO_2$ removal can decrease or end, while treatment with concentrated oxygen via the mask 25', 25" may be increased with a goal of eventually decreasing to a level at or below the patient's needs prior to the acute respiratory event. The patient, therefore, may be weaned gradually from the preferred systems 100, 100', 100" by employing and withdrawing portions of the treatments as the patient's condition improves.

Modularity of the preferred systems 100, 100', 100" can be achieved with the goal of each of the preferred systems 100, 100', 100" being configured to operate independently or concurrently utilizing each of the described treatment options or diminishing in size and complexity with the medical needs of the patient by operating select systems and modules during operation, as directed by the central processor 28. In addition to the above-described module function options, for example, an expansion manifold 70 may be located fluidly in line between the product manifold 18 and the sensor 22. The preferred expansion manifold 70 includes a port or releasable connection point 71 that is releasably sealable. The expansion manifold 70 preferably configured to facilitate gas flow from the product manifold 18, through the expansion manifold 70 and into the $CO_2$/oxygenation module 11 and its first and/or second membranes 19a, 19b when the expansion manifold 70 is open. Alternatively, the expansion manifold 70 may be actuated by the central processor 28 such that a conduit connected to the releasable connection point 71 is open, such that the fluid channel of the expansion manifold 70 to the $CO_2$/oxygenation module 11 is sealed and the concentrated oxygen gas is redirected into the mask 25', 25" via a conduit connected to the mask 25', 25" and the releasable connection point 71.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A readily transportable extracorporeal system for lung assist of a patient, the transportable extracorporeal system comprising:

a housing for enclosing at least a portion of the system;

arms extending from the housing, the arms configured to elevate the housing above the patient to reduce pressure on the patient and allow repositioning of the housing relative to the patient during use;

a blood flow inlet comprised of an inlet cannula in fluid connection with the housing;

a blood flow outlet comprised of an outlet cannula in fluid connection with the housing;

a $CO_2$/oxygenator module including a plurality of hollow gas permeable fibers configured to permit diffusion of gas between the patient's blood that flows between the blood flow inlet and the blood flow outlet and an interior of the hollow gas permeable fibers, the plurality of hollow gas permeable fibers positioned between the blood flow inlet and the blood flow outlet such that blood flows around the plurality of hollow gas permeable fibers, the plurality of hollow gas permeable fibers extending generally perpendicular to a direction of bulk flow of blood through the CO$_2$/oxygenator module, the plurality of hollow gas permeable fibers comprising a gas transfer membrane;

a gas inlet in fluid connection with the housing and in fluid connection with inlets of the plurality of hollow gas permeable fibers;

a gas outlet in fluid connection with the housing and in fluid connection with outlets of the plurality of hollow gas permeable fibers;

a first moving element to create velocity fields in blood flow contacting the plurality of hollow gas permeable fibers, the first moving element comprised of a pump;

a concentrated oxygen generating device, the oxygen generating device configured to generate concentrated oxygen from air, the oxygen generating device having a first outlet port and a first inlet port, the first outlet port being in fluid connection with the gas inlet, the first inlet port being in fluid connection to the gas outlet, the concentrated oxygen generating device configured to recycle waste oxygen from the gas transfer membrane to increase throughput and remove by an adsorption/desorption process, unwanted gasses;

a second moving element for moving gases, fluids and vapors, the second moving element having an intake port and an outtake port, the second moving element comprised of a compressor;

a hollow transport conduit having a proximal opening and a distal opening, the proximal opening in fluid connection with the outtake port; and a power source configured to provide power to the first and second moving elements.

2. The transportable extracorporeal system of claim 1, wherein the concentrated oxygen generating device includes a first adsorbent, a second adsorbent and a third adsorbent, the unwanted gasses being comprised of carbon dioxide, argon, water vapor, and nitrogen.

3. The transportable extracorporeal system of claim 1, wherein the concentrated oxygen generating device includes a sieve module, the sieve module including layers of zeolite material for adsorbing nitrogen, carbon dioxide and argon.

4. The transportable extracorporeal system of claim 3, wherein the sieve module is comprised of a first module, a second module and a third module.

5. The transportable extracorporeal system of claim 4, wherein the first, second and third sieve modules are removably mountable to the housing.

6. The transportable extracorporeal system of claim 1, further comprising:
a central processor in communication with the concentrated oxygen generating device, the first moving element and the second moving element.

7. The transportable extracorporeal system of claim 6, wherein the central processor is in communication with a plurality of sensors.

8. The transportable extracorporeal system of claim 7, wherein the plurality of sensors include a battery power sensor, a pressure sensor, a flow sensor, an oxygen sensor, a GPS tracker and an operation time sensor.

9. The transportable extracorporeal system of claim 1, wherein the power source is comprised of a battery.

10. The transportable extracorporeal system of claim 9, wherein the battery is removable and replaceable from the housing, the battery being rechargeable.

11. The transportable extracorporeal system of claim 1, further comprising:
a blower mounted to the housing;
a hose extending from the blower; and
a mask attached to the hose, the mask positionable on the patient's face to provide continuous positive airway pressure to the patient.

12. The transportable extracorporeal system of claim 1, wherein the arms are movable from an extended position, wherein the arms extend generally perpendicularly from the housing, to a folded position, wherein the arms are positioned adjacent to the housing.

13. The transportable extracorporeal system of claim 12, wherein the arms are pivotable from the extended position to the folded position.

14. The transportable extracorporeal system of claim 1, wherein the gas transfer membrane includes a first membrane and a second membrane.

15. The transportable extracorporeal system of claim 1, further comprising:
a belt fastening system connected to the housing and configured to attach the housing to the patient.

16. The transportable extracorporeal system of claim 1, wherein the concentrated oxygen generating device includes a product manifold, a first sieve column and a second sieve column, the first and second sieve columns removable and replaceable from the product manifold.

17. The transportable extracorporeal system of claim 16, wherein the first and second sieve columns include a first adsorbent, a second adsorbent and a third adsorbent therein.

18. The transportable extracorporeal system of claim 17, wherein the first adsorbent is comprised of a silver exchanged zeolite adsorbent, the second adsorbent is comprised of lithium exchanged zeolite adsorbent and the third adsorbent is comprised of a 5A-type zeolite adsorbent.

19. The transportable extracorporeal system of claim 1, wherein the plurality of hollow gas permeable fibers extend generally perpendicular to a direction of bulk flow of the patient's blood through the CO$_2$/oxygenator module.

* * * * *